United States Patent
Kawashima et al.

[11] Patent Number: 5,951,971
[45] Date of Patent: Sep. 14, 1999

[54] OPHTHALMIC COMPOSITIONS

[75] Inventors: Yoichi Kawashima, Kyoto; Mitsuaki Kuwano, Toyonaka, both of Japan

[73] Assignee: Novartis AG, Basel, Switzerland

[21] Appl. No.: 08/767,610

[22] Filed: Dec. 17, 1996

Related U.S. Application Data

[63] Continuation of application No. 08/331,648, filed as application No. PCT/EP93/01123, May 7, 1993, abandoned.

[30] Foreign Application Priority Data

May 13, 1992 [GB] United Kingdom ............... 9210226
Nov. 20, 1992 [GB] United Kingdom ............... 9224367

[51] Int. Cl.$^6$ .............................. A61K 47/14; A61K 9/66
[52] U.S. Cl. ........................................ 424/78.04; 514/885
[58] Field of Search ..................... 424/78.04; 514/885

[56] References Cited

U.S. PATENT DOCUMENTS

| | | | |
|---|---|---|---|
| 3,947,573 | 3/1976 | Rankin | 424/78.04 |
| 4,029,817 | 6/1977 | Blanco et al. | 424/78.04 |
| 4,649,047 | 3/1987 | Kaswan | 514/885 |
| 5,342,625 | 8/1994 | Hauer et al. | 424/455 |
| 5,525,590 | 6/1996 | Bollinger et al. | |

FOREIGN PATENT DOCUMENTS

| | | |
|---|---|---|
| 2211848 | 7/1989 | United Kingdom . |
| WO 93/20833 | 10/1993 | WIPO . |

*Primary Examiner*—Peter F. Kulkosky
*Attorney, Agent, or Firm*—Gabriel Lopez

[57] ABSTRACT

An ophthalmic composition particularly in the form of eye-drops suitable for the treatment of diseases of the eye and surrounding areas. The composition contains a cyclosporin and a surfactant selected from polyoxyethylene fatty acid esters, polyoxyethylene alkylphenyl ethers and polyoxyethylene alkyl ethers, or mixtures thereof.

10 Claims, No Drawings

OPHTHALMIC COMPOSITIONS

This is a continuation of application Ser. No. 08/331,648, filed Nov. 10, 1994 now abandoned which is a 371 of PCT/EP93/01123 filed May 7, 1993.

This invention relates to ophthalmic compositions, particularly eye-drop formulations, comprising a cyclosporin as active ingredient and being suitable for the treatment of diseases of the eye and surrounding areas.

The cyclosporins comprise a large and recognized class of peptide compounds having pharmaceutical utility, for example immunosuppressant, anti-inflammatory, and/or anti-parasitic activity and/or activity in abrogating tumor resistance to anti-neoplastic or cytostatic drug therapy. The cyclosporins include, for example, naturally occurring fungal metabolites, such as the cyclosporin A, B, C, D and G, as well as a wide variety of synthetic and semi-synthetic cyclosporins, for example the dihydro- and iso-cyclosporins (see e.g. U.S. Pat. Nos. 4,108,985; 4,210,581 and 4,220,641), [(D)-Ser]$^8$-Ciclosporin (see U.S. Pat. No. 4,384,996), [O-acetyl, (D)-Ser]$^8$-Ciclosporin (see U.S. Pat. No. 4,764,503), [β-fluoro-(D)Ala]$^8$-Ciclosporin (see UK Patent Application 2,206,119A), [Val]$^2$-[(D)methylthio-Sar]$^3$- and [Dihydro-MeBmt]$^1$-[Val]$^2$-[(D)methylthio-Sar]$^3$-Ciclosporin [see U.S. Pat. No. 4,703,033], [O-(2-hydroxyethyl)-(D)Ser]$^8$-Ciclosporin, and [3'-deshydroxy-3'-keto-MeBmt]$^1$-[Val]$^2$-Ciclosporin and many more.

Of the cyclosporins, the most widely investigated to date is cyclosporin A, being commercially available under the Registered Trade Mark SANDIMMUN or SANDIMMUNE. Cyclosporin A has been shown to suppress selectively a variety of T-lymphocyte functions, including prevention of maturation and expression of sensitized T-lymphocytes in cell mediated immune responses, and is now successfully and widely used in the suppression of organ transplant rejection. Cyclosporin A has also been used systemically in the treatment of intraocular inflammatory or autoimmune diseases, such as uveitis. However, because of the side effects associated with systemic therapy, Cyclosporin A has had only limited use in treating conditions of the eye.

Effective topical administration of Cyclosporin A to the eye would reduce or eliminate to a large extent the systemic side effects by restricting activity to the locus of the condition being treated and proposals to this effect have been made, (see for example U.S. Pat. No. 4,649,047). However, utility and effectiveness of Cyclosporin A in treating diseases and conditions of the eye has been hindered until now by the lack of suitable eye-drops which are acceptable to the eye. Eye-drops are required which do not cause patient discomfort and which permit a convenient administration regimen and do not require unduly frequent administration, while providing adequate drug substance delivery both to the external and, in particular, the internal regions of the eye. A further difficulty is the very poor solubility of cyclosporin A in water. This leads often to precipitation of cyclosporin A from aqueous-based eye-drops causing strong irritation of the eye.

Efforts have been made to overcome these difficulties by dissolving cyclosporin A in vegetable oils (Ophthalmology, 96, 1144–1150 (1989)) and by clatherating cyclosporin A with cyclodextrin (Japanese unexamined Patent Publication SHO-64-85921/1989).

In oily solution, however, cyclosporin A is poorly distributed in the eyes (Folia Ophthalmologica Japonica, 40, (5), 902–908 (1989)), and a high concentration (2%) of cyclosporin A is needed for clinical treatment (Ophthalmology, 96 1144–1150 (1989)). Further, these oily eye drops tend to cause a disagreeable feeling to the eyes.

Also, whereas cyclosporin eye-drops solubilized by clatherating with cyclodextrin certainly have an improved distribution in the eyes (Folia Ophthalmologica Japonica, 40 (5), 902–908 (1989)), the dissolved cyclosporin A is however again precipitated. As indicated by experiments in rabbits, this provokes strong irritation in at least the anterior part of eyes and induces redness and edema of conjunctival palpebrae and secretion from the conjunctiva, causing problems for application of cyclosporin A in this form.

There is thus an urgent need to develop a topical, ophthalmic formulation which causes less irritation to the eyes, has a better distribution of cyclosporin A in the eyes and has no problems of precipitation of cyclosporin.

In an attempt to solve these problems, studies have been conducted with various surfactants which are currently used for formulating medical substances with low solubility in water, especially the most commonly used surfactants polysorbate 80 and polyoxyethylene hydrogenated castor oil. However, polysorbate 80 was found to have a poor solubilizing effect, when used for the preparation of eye-drops, and the dissolution of cyclosporin was not sufficient. Polyoxyethylene hydrogenated castor oil was found to strongly irritate the eyes when used in eye-drops.

Thus these commonly used surfactants proved not to be successful for the preparation of eye-drops which contain a high concentration of cyclosporin and have decreased irritation to the eyes.

Surprisingly these difficulties may be overcome by formulating the cyclosporin in a surfactant selected from polyoxyethylene fatty acid esters, polyoxyethylene alkylphenyl ethers, and polyoxyethylene alkyl ethers, or mixtures thereof.

Accordingly in one aspect this invention provides an ophthalmic composition comprising a cyclosporin, especially cyclosporin A, and a surfactant selected from polyoxyethylene fatty acid esters, polyoxyethylene alkylphenyl ethers, and polyoxyethylene alkyl ethers, or mixtures thereof.

The ophthalmic compositions are preferably formulated as eye-drop formulations. Preferably they are aqueous based.

With these ophthalmic compositions, very good therapeutic results may be obtained even when the cyclosporin is present in low concentrations; for example within the range of from about 0.005 to about 1.0% (w/v), preferably about 0.005 to about 0.1% (w/v), and, more desirably from about 0.01 to about 0.075% (w/v). As used in this specification, 1% (w/v) is equivalent to 1 g per 100 ml.

Preferred polyoxyethylene fatty acid esters are based on saturated fatty acids, preferably not containing any substituent. The chain length may be from 14 to 22 carbon atoms, preferably 16 to 18 carbon atoms. A preferred fatty acid is stearate. Preferably the ester is a mono ester. Preferably the polymerization number of the polyoxyethylene moiety is from about 20 to about 60. A preferred example is polyoxyl 40 stearate. An example is the polyoxyl 40 stearate known under the brand name Myrj 52 (available from Atlas Chemie, Essen, Germany).

Preferred polyoxyethylene aralkyl esters are based on a phenol substituted by one or more alkyl groups; the alkyl groups for example having from 4 to 10 carbon atoms, preferably 8 or 9 carbon atoms. Preferably the phenyl group has only one alkyl group as substituent. Preferably the polymerization number of the polyoxyethylene moiety is from about 1 to about 50, more preferably around 40. A preferred example has properties as laid down in the Cosmetic, Toiletry & Fragrance Association, Inc (CTFA)

cosmetic ingredients directory. Examples are octoxynols, for example those known under the brand name "Triton" and obtainable from Rohm and Haas, Philadelphia, USA.

Preferred polyoxyethylene alkyl ethers are based on fatty alcohols having, for example, from 4 to 20 carbon atoms. Preferably the polymerization number of the polyoxyethylene moiety is from 10 to 60. An example is the polyoxyethylene alkyl ether known as Cetomacrogol 1000 which has an acid value of less than 0.5 a hydroxyl value of 40 to 52.5 and an refractive index of 1.448 to 1.452.

The preferred surfactant is a polyoxyethylene fatty acid ester and more preferably polyoxyl 40 stearate.

Preferably the weight ratio of surfactant to cyclosporin is from about 10:1 to about 50:1.

The concentration of surfactant in the ophthalmic compositions is desirably within the range of from about 0.1% to about 3.0% (w/v), and, more desirably from about 0.15 to about 2.5% (w/v), and especially 0.75% to 2.5% (w/v).

The ophthalmic composition may also include thickening (viscosity-increasing or viscoelastic) agents since these agents are useful for improving the distribution of the cyclosporin in the eyes. Preferred thickening agents are cellulose and cellulose derivative thickening agents such as alkyl celluloses and hydroxyalkylcelluloses and also non-cellulose thickening agents such as carboxyvinyl polymers, polyvinyl polymers and polyvinylpyrrolidones. Suitable examples are methyl cellulose, and especially hydroxypropyl methylcellulose 8 for example Nos. 2208 or 2906 as defined in the Japanese and US Pharmacopeia), and hydroxyethyl cellulose. Suitable polyvinyl polymers are polyvinylacetates and polyvinylalcohols and suitable polyvinylpyrrolidones are poly-N-vinylpyrrolidones and vinylpyrrolidone co-polymers such as vinylpyrrolidone-vinylacetate co-polymers.

The concentration of the thickening agents to be used is not critical. Typically it is within the range of about 0.05 to about 5.0% (w/v), and more desirably, from about 0.1 to about 3.0% (w/v).

To ascertain the distribution of the cyclosporin in the eyes, eye-drops containing cyclosporin A and a thickening agent were applied to rabbits. An eye-drop preparation in which cyclosporin A was solubilized with cyclodextrin was used as the control. The test showed that the eye-drops containing the thickening agent attained 1.7 times higher cyclosporin A concentration in the cornea than that obtained with the control.

With the excellent distribution of cyclosporins in the eyes obtained by the ophthalmic compositions, it is possible to obtain sufficient therapeutic efficacy of cyclosporins A in the eye-drops even at low concentrations of cyclosporins in the composition.

Preferably an anti-oxidant is present but this is not essential. The choice of anti-oxidants which may be used is not critical but it is desirable to use butylated hydroxyanisol or ascorbic acid, and preferably sodium thiosulfate or butylated hydroxytoluene. Also, instead of an anti-oxidant, the ophthalmic composition may be stored in a container containing nitrogen and optionally including a free oxygen absorber (for example, Fe).

Stability studies were conducted using butylated hydroxytoluene as a representative anti-oxidant. In the studies it was found that the amount of cyclosporin (especially cyclosporin A) present after storage for one month at 40° C. without anti-oxidant was reduced down to 85.3%. On the other hand there was no significant loss of cyclosporin in the composition containing an anti-oxidant as defined above. This showed extremely high stability. For example the composition of Example 5D as described hereinafter showed no appreciable decomposition after 3 months at 25° C. and 40° C. However not all compositions require an anti-oxidant for stability.

Naturally the anti-oxidant should be present at concentrations below which it causes irritation of the eyes. Typically the concentration of anti-oxidant should be within the range from about 0.00005 to about 0.1% (w/v), more desirably within the range of from about 0.0001 to about 0.01% (w/v) to avoid irritation of the eye.

The preferred ophthalmic composition comprises from about 0.01 to about 0.075% (w/v) of cyclosporin A; from about 0.15 to about 2.5% (w/v) of polyoxyl 40 stearate; from about 0.1 to about 3.0% (w/v) of a cellulose thickening agent selected from hydroxypropyl methylcellulose or hydroxyethylcellulose; and from about 0.0001 to about 0.01% (w/v) of an anti-oxidant selected from butylated hydroxytoluene or sodium thiosulfate.

The combination of the surfactants such as polyoxyl 40 stearate or polyoxyethylene cetyl ether or polyoxyethylene octylphenyl ether with a cyclosporin (especially cyclosporin A) yields an excellent eye-drop preparation causing less irritation to the eyes, providing better distribution in the eyes, having a low concentration of cyclosporin A minimizing the problem of its precipitation, and yet having higher stability. Moreover the inclusion of an anti-oxidant and an cellulose thickening agent may further improve the distribution of the cyclosporin in the eyes and the stability.

If desired other excipients may be present, for example an isotonic agent, buffer, preservative, and/or pH-controlling agent. Sterile purified water in appropriate amounts may be present to obtain the desired eye-drop preparation.

Conveniently ethanol is present, for example at a concentration of about 0.01 to 0.5% (w/v).

The pH of the ophthalmic composition may be within the range which is normally used for ophthalmic preparations, but is desirably within the range of 4 to 8.

The ophthalmic compositions may be prepared by mixing the cyclosporin with the above-mentioned surfactant, and as desired mixing in the thickening agent and the anti-oxidant, and other excipients.

The ophthalmic compositions may be filled in appropriate containers to facilitate administration to the eye, for example a dropper fitted with a suitable pipette.

Accordingly, in another aspect this invention provides an ophthalmic composition as defined above in a container appropriate for ophthalmic application of the composition, for example appropriate for application of the ophthalmic composition to or at the surface of the eye (for example to the cornea or corneal epithelium).

The invention also provides a method of treating a disease or condition of the eye or of the surrounding or associated organs or tissues, in a subject in need thereof, in particular of treating immune mediated or inflammatory diseases organs or tissues, which method comprises administering an ophthalmic composition as defined above topically to the eye, for example to or at the surface of the eye (for example to the cornea or corneal epithelium). The particular sections, segments or tissues of the eye to which the method is applicable are as described in this specification. Particular diseases or conditions of the eye to which the method is applicable are similarly as described in this specification.

In a further aspect the invention provides an ophthalmic composition as defined above for use in a method as defined above.

In another aspect this invention provides the use of a cyclosporin in the preparation of an ophthalmic composition for use in a method as defined above.

The following examples are illustrative of ophthalmic compositions of the invention. Further details of components are given in "Lexicon for Pharmazie, Kosmetic and angrenzende Gebiete" by H. P. Fiedler, 3rd Edition, 1989 published by Editio Cantor Aulendorf, Germany; Handbook of Pharmaceutical Excipients, 1st Edition, 1986, joint publication of American Pharmaceutical Association, Washington, USA and the Pharmaceutical Society of Great Britain, London, England; or from the relevant manufacturers. In the following examples, viscosity is measured as Newton viscosity at 25° C., for example measured in a viscosity measuring apparatus type CV 20 produced by HAAKE.

The polyoxyl 40 stearate used in the Examples is KIKKOL (Registered Trade Mark) MYS-40, a product of Nikko Chemicals Co. Ltd. Japan. It has a congealing point of 39 to 44° C., an acid value of not more than 1 and a saponification value of 25 to 35.

The polyoxyethylene octyl phenyl ether used in the Examples is NONION HS 240, a product of Nippon Oil and Fats Co. Ltd., Japan. The mean polymerization number is 40 and the mean molecular weight is 1968.

The hydroxy propyl methylcellulose (also referred to as HPMC) used in the Examples is METOLOSE 65SH-4000 a product of Shin-Etsu Chemical Co. Ltd. Japan, corresponding to hydroxypropyl methyl cellulose 2906.

EXAMPLE 1

Eye-drop formulation (in 100 ml)

| | | |
|---|---|---|
| Cyclosporin A | 0.05 | g |
| Polyoxyl 40 stearate | 2.0 | g |
| Hydroxypropyl methylcellulose | 0.3 | g |
| Butylated hydroxytoluene | 0.001 | g |
| Ethanol | 0.1 | g |
| Sodium chloride | 0.73 | g |
| Sodium dihydrogen phosphate | 0.2 | g |
| Sodium edethate | 0.1 | g |
| Sodium hydroxide | q.s. | |
| Sterile purified water | q.s. | |

Method for preparation:

The cyclosporin A is dissolved in an ethanolic solution containing the butylated hydroxytoluene, and the polyoxyl 40 stearate is added to it. After warming the mixture, the hydroxypropyl methylcellulose (which is dissolved in advance into a small amount of sterilized purified water) is added and the remaining sterile purified water is added to the mixture to yield a clear solution. Lastly, the sodium chloride, sodium dihydrogen phosphate and sodium edethate is added to the mixture, and the pH is adjusted to 6.0 using sodium hydroxide solution.

The following formulations can be prepared in the same manner as mentioned above.

EXAMPLE 2

Eye-drop formulation (in 100 ml)

| | | |
|---|---|---|
| Cyclosporin A | 0.025 | g |
| Polyoxyl 40 stearate | 0.5 | g |
| Hydroxypropyl methylcellulose | 0.2 | g |
| Butylated hydroxytoluene | 0.0005 | g |
| Ethanol | 0.1 | g |
| Sodium chloride | 0.73 | g |
| Sodium dihydrogen phosphate | 0.2 | g |
| Sodium edethate | 0.1 | g |
| Sodium hydroxide | q.s. | |
| Sterile purified water | q.s. | |

EXAMPLE 3

Eye-drop formulation (in 100 ml)

| | | |
|---|---|---|
| Cyclosporin A | 0.075 | g |
| Polyoxyl 40 stearate | 2.5 | g |
| Hydroxypropyl methylcellulose | 0.2 | g |
| Butylated hydroxytoluene | 0.002 | g |
| Ethanol | 0.1 | g |
| Sodium chloride | 0.73 | g |
| Sodium dihydrogen phosphate | 0.2 | g |
| Sodium edethate | 0.1 | g |
| Sodium hydroxide | q.s. | |
| Sterile purified water | q.s. | |

EXAMPLE 4

Eye-drop formulation (in 100 ml)

| | | |
|---|---|---|
| Cyclosporin A | 0.1 | g |
| Polyoxyl 40 stearate | 3.0 | g |
| Hydroxyethyl cellulose | 0.3 | g |
| Sodium thiosulfate | 0.01 | g |
| Ethanol | 0.1 | g |
| Sodium chloride | 0.73 | g |
| Sodium dihydrogen phosphate | 0.2 | g |
| Sodium edethate | 0.1 | g |
| Sodium hydroxide | q.s. | |
| Sterile purified water | q.s. | |

EXAMPLE 5

| | A | B | C* | D |
|---|---|---|---|---|
| Cyclosporin A | 0.075% | 0.075% | 0.05% | 0.05% |
| Polyoxyl 40 stearate | 1.125% | 1.125% | 0.75% | 1% |
| HPMC | — | — | 0.3% | 0.3& |
| Butylated hydroxy-toluene | — | — | — | 0.0001% |
| Propylene glycol | — | 0.25% | — | — |
| Ethanol | 0.1% | — | 0.1% | 0.1% |
| Concentrated glycerin | 2.1% | 1.92% | — | — |
| $NaH_2PO_4 \cdot 2H_2O$ | 0.2% | 0.2% | 0.2% | 0.2% |
| Sodium edethate | — | — | 0.1% | 0.1 |
| NaCl | — | — | 0.72% | 0.72% |
| HCl/NaOH (to pH 7) | q.s. | q.s. | — | — |
| Purified water | q.s. | q.s. | q.w. | q.w. |

* Viscosity 6.2 cps

In the above examples the polyoxyl 40 stearate may be replaced by an equivalent amount of polyethylene octyl phenyl ether or polyoxyethylene alkyl ether.

The ophthalmic compositions are useful for the same indications as other topical ophthalmic compositions containing cyclosporins, for example diseases affecting the cornea, the aqueous, the lens, the iris, the ciliary, the choroid or the retina. The ophthalmic compositions are useful particularly for the treatment of an autoimmune or inflammatory disease or condition of the eye or of the surrounding or associated organs or tissues, that has undesirably elevated immuno-response or inflammatory reaction or event as part of its etiology. The ophthalmic compositions are useful preferably for treating the anterior or posterior segment of the eye. For example for the treatment of anterior or posterior uveitis, chronic keratititis, keratoconjunctivitis sicca, vernal keratoconjunctivitis, conjunctivitis, including vernal conjunctivitis, or in keratoplasty. The ophthalmic compositions may also be used in the treatment of immnunoreactive graft rejection post corneal transplantation, Behçet disease, and autoimmune corneal diseases such as Mooren's ulcer, ocular pemphigus, and rheumatoid ulcer.

The utility of the ophthalmic compositions and advantageous therapeutic properties can be observed in standard animal models and in standard clinical tests; for example by administering, a few times a day, 0.05 ml to 0.5 ml, preferably 0.1 ml to 0.2 ml, of an ophthalmic composition containing 0.005% to 1.0%, preferably 0.01% to 0.5%, (by weight) of cyclosporin to the eyes of patients exhibiting diseases or conditions of the eye as set forth above. The tolerance of and transfer of the cyclosporin into the eye may be shown in tests as described below.

The optimal dosage to be administered to a particular patient will vary from patient to patient and from disease to disease and must be considered carefully by the treating physician. However doses in the range of 0.05 ml to 0.5 ml, preferably 0.1 ml to 0.2 ml, of an ophthalmic composition containing 0.005% to 1.0%, preferably 0.01% to 0.5%, (by weight) of cyclosporin may be used. Satisfactory results are obtained by administering droplets of about 0.05 ml a few times a day; for example 1 to 5 times a day.

The excellent tolerance of the ophthalmic compositions may be determined in conventional tests. For example the compositions are administered topically to groups of 6 rabbits. One drop (about 50 microliter) at a time is instilled intra-ocularly into one eye, every 30 minutes, for 5 hours (ten administrations). The other eye (untreated) is used as a control. The eye is then examined microscopically for irritation at 1, 5 and 18 hours after the final administration, and the effect of the composition judged with respect to: opacity and opaque area in the cornea; the iris, redness and edema of conjunctival palpebrae, redness of conjunctival bulbi, state of mictating membrane and secretion of conjunctiva.

The ophthalmic compositions show excellent tolerability. For example the compositions of Examples 5A and B showed a zero score in all the above mentioned evaluations, except for the evaluation of redness of conjunctival palpebrae. In this evaluation, however, only a marginal redness of conjunctival palpebrae was noted at 1 hour after final administration and the results are very close or identical to results obtained with physiological saline (0.9% sodium chloride).

The transfer of Cyclosporin A into the cornea (without epithelium) from the ophthalmic compositions may be evaluated by conventional tests. In one test 50 microliters of test solution are installed into the eyes of groups of 5 rabbits and the amount of Cyclosporin A in the cornea measured. The animals are sacrificed by injection of sodium pentobarbital through the auditory vein 30 minutes after administration. The eye balls are enucleated, their surface cleaned with 1 ml of physiological saline and the corneal epithelium removed with a fine razor. The cornea is then resected by cutting it along its circumference, and washing it 3 times with physiological saline and drying it completely free of water using a sheet of filter paper. The cornea is weighed, and kept at −80° C.

The cornea is then homogenized in 1 ml methanol while cooling with ice and the homogenate centrifuged at 3000 rpm for 10 minutes at room temperature. The supernatant is collected. 1 ml methanol are added, the mixture subjected to Boltex treatment and then centrifuged again. The supernatants are combined, evaporated at 40° C. to 50° C. and 1 ml methanol is added to the residue. 50 microliters of the solution are measured out and the amount of Cyclosporin A therein determined by standard radioimmunoassay procedures.

The excellent transfer of Cyclosporin A into the cornea is for example shown by the composition of Example 5C in the above test. A mean value of 479.2 ng/g (S.D. +/−245.8) is observed.

For the purpose of such trials, or for practical therapeutic use, the ophthalmic compositions (for example the composition of example 1) are suitably administered at or to the surface of the eye in individual amounts. For example of from about 0.1 to 0.2 ml from 1 to 4×daily, depending upon the particular disease or condition to be treated, its clinical status and the effect desired. Marked improvement in condition as compared with untreated controls are observable with continuance of treatment, for example over a period of 1 to 2 weeks and upwards. The ophthalmic compositions are found to be well tolerated by subjects undergoing such therapy, with no significant or untoward irritation.

We claim:

1. An oil-free ophthalmic composition comprising:
   (A) a cyclosporin,
   (B) a surfactant selected from the group consisting of polyoxyethylene fatty acid esters, polyoxyethylene alkylphenyl ethers, and polyoxyethylene alkyl ethers, or mixtures thereof in an amount of from about 0.1% to about 3.0% (w/v); and
   (C) purified water
   the cyclosporin being in solution at a concentration of from about 0.01 to about 0.075% (w/v).

2. An ophthalmic composition of claim 1, further comprising a thickening agent.

3. An ophthalmic composition of claim 2 in which the thickening agent is selected from cellulose thickening agents, carboxyvinyl polymers, polyvinyl polymers, and polyvinylpyrrolidones.

4. An ophthalmic composition of claim 1 comprising:
   1) from about 0.01 to about 0.075% (w/v) of cyclosporin A;
   2) from about 0.15 to about 2.5% (w/v) of polyoxyl 40 stearate;
   3) from about 0.1 to about 3.0% (w/v) of a cellulose thickening agent selected from hydroxypropyl methylcellulose and hydroxyethylcellulose; and
   4) from about 0.0001 to about 0.01% (w/v) of an antioxidant selected from butylated hydroxytoluene and sodium thiosulfate.

5. An ophthalmic composition of claim 1 in which the cyclosporin is cyclosporin A.

6. An ophthalmic composition of claim 1 in a container appropriate for topical ophthalmic application of the composition.

7. A method of treating an autoimmune or inflammatory disease or condition of the eye or of the surrounding or associated organs or tissues in a subject in need thereof, which method comprises administering to said subject a composition of claim 1 topically to the eye.

8. An ophthalmic composition of claim 1 for use in a method of treating an autoimmune or inflammatory disease or condition of the eye or of the surrounding or associated organs or tissues in a subject in need thereof.

9. A method of claim 7 for treating an autoimmune disease or condition.

10. A method of claim 7, which comprises the suppression of organ transplant rejection.

* * * * *

UNITED STATES PATENT AND TRADEMARK OFFICE
CERTIFICATE OF CORRECTION

PATENT NO. : 5,951,971
DATED : September 14, 1999
INVENTOR(S) : Kawashima et al.

It is certified that error appears in the above-identified patent and that said Letters Patent is hereby corrected as shown below:

Column 8,
Line 25, after the word "esters" insert -- wherein the polymerization number of the polyoxyethylene moiety is from about 20 to about 60 --.

Signed and Sealed this

Twenty-fourth Day of July, 2001

Attest:

NICHOLAS P. GODICI
Attesting Officer
Acting Director of the United States Patent and Trademark Office